United States Patent [19]

Friedman et al.

[11] Patent Number: 5,811,253
[45] Date of Patent: Sep. 22, 1998

[54] USE OF VANADIUM BROMOPEROXIDASE AS A SIGNAL-GENERATING ENZYME FOR CHEMILUMINESCENT SYSTEMS: TEST KITS AND ANALYTICAL METHODS

[75] Inventors: Alan Eric Friedman, Rochester; Sarah Fingar Groulx, Ontario, both of N.Y.; Alison Butler, Santa Barbara, Calif.

[73] Assignee: Johnson & Johnson Clinical Diagnostics, Inc., Rochester, N.Y.

[21] Appl. No.: 522,604

[22] Filed: Sep. 1, 1995

[51] Int. Cl.$^6$ .................................................. C12Q 1/28
[52] U.S. Cl. ............................... 435/28; 435/25; 435/7.9; 435/7.91
[58] Field of Search ...................... 435/6, 28, 7.9, 435/7.91, 91.2, 4, 25; 544/236; 546/141

[56] References Cited

U.S. PATENT DOCUMENTS

| | | |
|---|---|---|
| 4,598,044 | 7/1986 | Kricka et al. . |
| 4,729,950 | 3/1988 | Kricka et al. . |
| 4,745,077 | 5/1988 | Holian et al. . |
| 4,950,588 | 8/1990 | Dattagupta .................................. 435/6 |
| 4,965,188 | 10/1990 | Mullis et al. ............................... 435/6 |
| 5,077,198 | 12/1991 | Shih et al. . |
| 5,082,780 | 1/1992 | Warren, III et al. . |
| 5,085,986 | 2/1992 | Mauck et al. . |
| 5,106,732 | 4/1992 | Kondo et al. . |
| 5,306,621 | 4/1994 | Kricka ................................... 435/7.91 |
| 5,324,835 | 6/1994 | Yamaguchi . |
| 5,332,662 | 7/1994 | Ullman .................................... 435/28 |
| 5,340,716 | 8/1994 | Ullman et al. ............................... 435/6 |
| 5,372,931 | 12/1994 | Friedman et al. .......................... 435/6 |
| 5,372,932 | 12/1994 | Friedman et al. ....................... 435/7.9 |
| 5,387,510 | 2/1995 | Wu ....................................... 435/91.2 |
| 5,420,275 | 5/1995 | Masuya et al. .......................... 544/236 |
| 5,424,194 | 6/1995 | Otigiri et al. ............................ 435/7.9 |
| 5,445,944 | 8/1995 | Ullman .................................... 435/28 |
| 5,476,939 | 12/1995 | Johnson ................................. 546/141 |
| 5,512,451 | 4/1996 | Kricka ..................................... 435/28 |
| 5,556,758 | 9/1996 | Allen ..................................... 435/7.9 |
| 5,616,719 | 4/1997 | Davalian et al. ....................... 546/334 |
| 5,618,732 | 4/1997 | Pease et al. ................................. 436/8 |

FOREIGN PATENT DOCUMENTS 91310875.9  11/1991  European Pat. Off. .
88/01302    2/1988   WIPO .

OTHER PUBLICATIONS

Butler et al., "Marine Haloperoxidases", Chem. Rev. 1993, 93, 1937–1944, Jul. 1993.
Butler et al., (1993), "Marine Haloperoxidases" Chem. Revs. 93, pp. 1937–1944.
de Boer et al., (1988), "N–coorination to Vo$^{2+}$ in reduced vanadium bromoperoxidase, and electron spin echo study", FEBS, 235, pp. 93–97.
Grunderman et al., (1987), "Chemiluminscence in organic Chemistry", Springer–Verlag, pp. 204–207.
Matthews et al., (1988), "Analytical Strategies for the Use of DNA Probes", Analytical Biochem., 169, pp. 1–25.
Rehder et al., (1987), "$^{51}$V NMR Investigation of a Vansdate (V)–dependent Peroxidase from Ascophyllum (L.) Le Jol" Inorganics Chimics Acts, 136, pp. L7–L10.
Weiss, (1991), "Hot Prospect for New Gene Amplifier" Science 254 pp. 1292–1293.
Wever et al., (1985), "Isolation procedure and some properties of the bromoperoxidase from the seaweed *Ascophyllum nodosum*" Biochimica et Biophysica Acta 830 pp. 181–186.
Yoshitake et al., (1979), "Conjugation of Glucose Oxidase from *Aspergillus niger* and Rabbit Antibodies Using N–Hydroxysuccinimide Ester of N–(4–Carboxycyclohexylmethyl)–Maleimide" Eur J.Biochem. 101, pp. 395–399.

*Primary Examiner*—John Kight
*Assistant Examiner*—Dameron Jones
*Attorney, Agent, or Firm*—Alan Morrison

[57] ABSTRACT

Aqueous compositions, test kits and methods can be used to detect hydrogen peroxide or vanadium bromoperoxidase by generating a chemiluminescent signal in the presence of the analyte. Signal generation as well as reaction kinetics are improved by using a composition which comprises a 2,3-dihydro-1,4-phthalazinedione derivative; a halogen, pseudohalogen, halogen-providing or pseudohalogen-providing source; and a peroxide or peroxide-generating reagent composition.

40 Claims, 4 Drawing Sheets

FIG. 2 ENHANCED HRP VS. UNENHANCED VBrPO; SIGNAL/NOISE

USE OF VANADIUM BROMOPEROXIDASE AS A SIGNAL-GENERATING ENZYME FOR CHEMILUMINESCENT SYSTEMS: TEST KITS AND ANALYTICAL METHODS

FIELD OF THE INVENTION

The present invention relates to a chemiluminescent composition, test kit, and method for the detection of various analytes using a vanadium bromoperoxidase as the signal-generating enzyme.

BACKGROUND OF THE INVENTION

It is well known to perform a quantitative or qualitative analysis of an aqueous liquid by contacting that liquid with a combination of reagents capable of producing a detectable output in proportion to the concentration of the analyte in the liquid. One type of useful assay utilizes enzymatic reactions wherein the analyte, upon contact with the appropriate reagents, reacts with oxygen in the presence of a suitable enzyme to produce hydrogen peroxide in proportion to the concentration of the analyte. A detectable product is then produced by the reaction of hydrogen peroxide in proportion to the concentration of the analyte in the test liquid. Analytes such as glucose, triglycerides, uric acid, cholesterol, and creatine kinase can be so detected. Peroxidase is generally used in these assays.

In other assays, a peroxidase is reacted in the presence of hydrogen peroxide which has been added to the system to measure the amount of a particular analyte. For example, such assays are represented by specific binding of ligands in specific binding assays wherein the peroxidase is used as a label. Such determinations can be carried out in solution, on a surface, or in diagnostic test devices. The signals produced in such assays can be either calorimetric, chemiluminescent, or fluorescent signals using well known signal-generating reagents.

There are several major types of peroxidase-dependent luminescent or luminometric assays which produce an emission of light as a result of the presence of the analyte of interest. These assays are also known as chemiluminescent assays and are described, for example, in U.S. Pat. No. 4,729,950 to Kricka et al. and the literature cited therein. Various aromatic amines and phenols, such as 4-iodophenol, are useful for enhancing the production of light in such assays (See U.S. Pat. No. 4,598,044 to Kricka et al.). U.S. Pat. No. 5,372,931 to Friedman et al. provides aqueous compositions which utilize certain 4'-hydroxy- and alkoxy-substituted phenyl or naphthyl electron transfer agents to enhance the generation of a signal.

Although the prior art enhanced peroxidase-dependent chemiluminescent systems produce adequate light signal for immunoassays, the prior art reagent formulations have certain known disadvantages. For example, reagent compositions including chemiluminescent enhancers as defined above are more complex and prone to storage instability. The need to critically control the activity of several reagents in prior art formulations presents considerable manufacturing problems.

Furthermore, prior art signal kinetics are a strong function of peroxidase level which can lead to non-linear calibration.

Recently, Butler and Walker have described a family of vanadium bromoperoxidases extracted from aquatic and marine algae and some from terrestrial lichens and fungi that, in the presence of hydrogen peroxide and bromide anion, catalytically produce activated bromine species which are potent oxidants. (See, Butler et al., Chem. Revs., 93, pp. 1937–1944, 1993 and references therein and Wever, et al. Biochem, Phys. Acta, 830, pp. 181–186, 1985 and references therein). Both of the aforementioned references are incorporated herein by reference.

One of the problems with most haloperoxidases is that their pH optima are generally in the lower pH range i.e., 3–5. This presents a problem with peroxidase-based chemiluminescent systems which depend upon a peroxy anion; hydroperoxides typically have a pKa of about 11.5. Vanadium bromoperoxidase works effectively in a pH range of about 6–10.

Although the aqueous signal-providing compositions disclosed in the prior art show remarkable behavior in many analytic systems, there is still a need for further improvements in this field. For example, there is still a need for providing a simpler signal-providing composition; i.e. one that does not use the electron transfer agents described in U.S. Pat. No. 5,372,931. Furthermore, there still is a need to develop an aqueous composition which has improved enzyme stability, greater sensitivity and improved signal output compared with the known prior art systems.

SUMMARY OF THE INVENTION

The need for further improvements in analytic compositions and methods has been met in the instant invention with an aqueous analytical composition, providing a chemiluminescent signal, having a pH of from about 6.5 to about 10. Specifically, the chemiluminescent signal-providing composition of the present invention having the above properties comprises:

(a) a chemiluminescent signal-generating reagent which provides a signal in response to the catalytic activity of a vanadium bromoperoxidase, said signal-generating reagent is a 2,3-dihydro-1,4-phthalazinedione derivative;

(b) a halogen, pseudohalogen, halogen-providing source or pseudohalogen-providing source; and (c) a peroxide or a peroxide-generating reagent composition.

The present invention also provides a diagnostic test kit for the determination of an analyte as the result of the catalytic activity of a vanadium bromoperoxidase. According to this embodiment of the instant invention, the diagnostic test kit comprises:

(i) the signal-providing composition described above, and (ii) a vanadium bromoperoxidase or a vanadium bromoperoxidase-labeled specific binding molecule.

According to another aspect of the instant invention, a method for producing a detectable signal in response to a vanadium bromoperoxidase is provided. Specifically, the method of the instant invention comprises:

(A) reacting a vanadium bromoperoxidase in the presence of the aforementioned signal-providing composition; and (B) determining the resulting chemiluminescent signal as a measure of the vanadium bromoperoxidase.

The instant invention further provides a specific binding assay for the determination of a specific binding ligand which comprises:

(A) complexing a specific binding ligand with a receptor specific for the ligand to form a specific binding complex;

(B) labeling the specific binding complex with a vanadium bromoperoxidase that is either conjugated with the receptor, or is conjugated with a specific binding molecule that is reactive with either the specific binding ligand or the receptor;

(C) after separating uncomplexed materials from the vanadium bromoperoxidase-labeled complex, contacting the complex with the above-described signal-providing composition; and (D) determining the resulting signal as a measure of the specific binding ligand.

The present invention provides all of the known prior art advantages associated with the use of various chemiluminescent assays; but utilizes various vanadium bromoperoxidase compounds in the reaction scheme. In addition to providing all the known prior art advantages, it should be further understood that by utilizing the signal-providing composition of the instant invention, the assays are more sensitive.

Moreover, the composition of the present invention demonstrates stable kinetics wherein the emitted light signal remains at a constant intensity for a longer period of time. Furthermore, the simpler composition of the instant invention eliminates a requirement for organic enhancer compounds.

DETAILED DESCRIPTION OF THE INVENTION

The present invention can be practiced to advantage in any analytical method designed to generate a chemiluminescent signal in response to the presence of a vanadium bromoperoxidase. Such assays can involve the detection of an organic or inorganic peroxide (such as hydrogen peroxide) or vanadium bromoperoxidase, or the detection of a non-immunological analyte other than vanadium bromoperoxidase or hydrogen peroxide. In particular, the invention is useful in the practice of specific binding assays which generate a chemiluminescent signal.

The assay can be qualitative or quantitative or both, and be used to detect a biological or chemical substance (that is, an analyte) in aqueous liquids, including human or animal biological fluids, waste fluids, foods, environmental effluents, chemical processing liquids and other specimens readily apparent to one skilled in the art.

Hydrogen peroxide (or another peroxide) can be determined with this invention. In addition, the invention can be used to determine analytes which are capable of producing hydrogen peroxide, that is the analyte participates in one or more reactions which produce hydrogen peroxide in the presence of a suitable signal-generating reagent and a vanadium bromoperoxidase. Such analytes are considered herein as "analytes catalytically related to a vanadium bromoperoxidase".

In a preferred embodiment, the signal-providing composition of the instant invention is useful for the determination of a specific binding ligand, or its corresponding receptor (that is, a substance which specifically binds with the ligand). Such ligands include, but are not limited to, antibodies, antibody fragments, and other proteins (including lipoproteins, blood proteins, enzymes and glycoproteins), haptens, drugs, hormones, steroids, toxins, viruses, bacteria, vitamins, saccharides (including polysaccharides), lipids, nucleic acids, nonproteinaceous blood components, or any components thereof readily understood by one skilled in the art.

As stated hereinabove, the present invention relates to an analytical composition for providing a chemiluminescent signal having a pH of from about 6.5 to about 10, said composition comprising:

(a) a chemiluminescent signal-generating reagent which provides a signal in response to the catalytic activity of a vanadium bromoperoxidase, wherein the signal-generating reagent is a 2,3-dihydro-1,4-phthalazinedione derivative;

(b) a halogen, pseudohalogen, halogen-providing source or pseudohalogen-providing source; and (c) a peroxide or peroxide-generating reagent composition.

As indicated above, the signal-providing composition of the instant invention contains, as one of its components, a 2,3-dihydro-1,4-phthalazinedione derivative (identified herein as "DPD"). Any free or conjugated DPD that can be converted to an excited state in a chemiluminescent reaction and then returns to a non-excited state with the emission of light, is useful in the practice of this invention. A considerable number of such compounds are known in the art, including those described in U.S. Pat. No. 4,598,044 to Kricka et al. and in Grundermann et al., Chemiluminescence in organic Chemistry, Springer-Verlag, Berlin, 1987, pages 204–207.

Such compounds are generally known as "luminol-type hydrazides" and include phthalic hydrazides, naphthalene-1,2-dicarboxylic acid hydrazides, anthracene-2,3-dicarboxylic acid hydrazides, phenanthrene-1,2-dicarboxylic acid hydrazides, fluorene-1,2-dicarboxylic acid hydrazides, benzo[g,h,i]-perylene-1,2-dicarboxylic acid hydrazides, coronene-1,2-dicarboxylic acid hydrazides, and others readily apparent to one skilled in the art.

In particular, the DPD's that can be employed in the instant invention are defined by the following structural formula:

wherein $Z^1$, $Z^2$, $Z^3$, and $Z^4$ are independently hydrogen; an alkyl containing from about 1 to about 6 carbon atoms such as methyl, ethyl, isopropyl, t-butyl, sec-pentyl and hexyl; an alkenyl containing from about 2 to about 6 carbon atoms such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl; a hydroxy;

an alkoxy containing from about 1 to about 6 carbon atoms such as methoxy, ethoxy, isopropoxy, t-butoxy and hexoxy; a carboxy, an amino including amino substituted with alkyl or alkanoyl, such as methylamino, ethylamino, amido (for example, acetamido and hexanamido), dimethylamino, diethylamino and diisobutylamino; a conjugated aminoalkenyl (for example, as defined below); or an aminoaryl including substituted aminoaryl, such as p-(N,N-dimethylamino)phenyl, p-(N,N-diethylamino)phenyl and 5-amino-2,3-dihydro-1,4-phthalazinedion-8-yl (also known as luminyl).

At least one of $Z^1$ and $Z^2$ is an amino (including substituted amino, as defined above), conjugated aminoalkenyl (including substituted aminoalkenyl as described above) or an aminoaryl such as p-(N,N-dimethylamino)-phenyl, p-(N,N-diethylamino)phenyl and 5-amino-2,3-dihydro-1,4-phthalazinedion-8yl. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group such as 2-(N,N-diisopropylamino)vinyl, 2-(N,N-diisobutylamino)vinyl and 2-(N,N-diisopentylamino)vinyl; and dialkylaminobutadienyl groups, such as 4-(N,N-diethylamino)-1,3-butadiene-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or an alkoxy having from about 1 to about 4 carbon atoms such as methoxy, ethoxy and isopropoxy. Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol (5-amino-2,3-dihydro-1,4-phthalazinedione) and isoluminol (6-amino-2,3-dihydro-1,4-phthalazinedione) are preferred, and luminol is most preferred.

Other useful classes of DPD compounds are described in the Gundermann et al. publication cited above, and include substituted or unsubstituted phthalic acid hydrazides, anthracene-2,3-dicarboxylic acid hydrazides, phenanthrene dicarboxylic acid hydrazides, fluorene-1,2-dicarboxylic acid hydrazides, benzo[g,h,i]perylene-1,2-dicarboxylic acid hydrazides and coronene-1,2-dicarboxylic acid hydrazides, such as those illustrated by the following structures:

and

Other phthalazinedione analogs recognized by those skilled in the art as being useful in this invention include those disclosed in European Patent Application No. 91310875.9 to Masuya et al. and U.S. Pat. No. 5,324,835 to Yamaguchi, the contents of which are incorporated herein by reference.

The compounds identified above can be obtained commercially, or be prepared using conventional starting materials and procedures well known to those skilled in the art.

The second component of the signal-providing composition of the instant invention is a halogen, pseudohalogen, halogen-providing source or pseudohalogen-providing source. The terms "halogen or halogen-providing source" as used herein denote any material which when added to the composition of the instant invention provides a halogen anion, i.e. a fluoride, chloride, bromide or iodide anion. This includes the halogens like chloride, bromide and iodide. The halogen-providing source may comprise a metal or non-metal salt including, but not limited to, ammonium, alkyl ammonium, substituted alkyl ammonium, aryl ammonium, substituted aryl ammonium, hydrazinium, oxonium, tropylium, sulfonium and the like. Typically, the halogen-providing source is added to the composition as a Group IA metal salt but is not limited to Group IA metal salts. In a highly preferred embodiment of the instant invention, the halogen-providing source is NaBr or ammonium bromide.

The terms "pseudohalogen or pseudohalogen-providing source" is used herein to denote any material which when added to the composition of the instant invention provides anions which have a high electron affinity that is comparable to the halogens. It should be noted that the pseudohalogen-providing source is typically, but not limited to, a Group IA metal compound. Suitable pseudohalogens that may be present in the analytical signal-providing composition include, but are not limited to, $CN^-$, $SCN^-$, $OCN^-$, azide, isonitrile and the like. Of the pseudohalogens, $SCN^-$ is particularly preferred.

The third component of the analyte composition of the instant invention is a peroxide or a peroxide-generating reagent composition. The term 'peroxide' includes inorganic or organic peroxide compounds that are typically employed in the prior art. By peroxide-generating reagent composition, it is meant to include any reagent composition which is capable of producing peroxide when added to the composition of the instant invention. Such peroxide-generating reagent compositions are well known to those skilled in this art and include, but are not limited to, perborates, peracetates, urea peroxide, and organic peroxides such as peracids, peroxybenzoic acid and oxones as well as hydroperoxides.

The analytic composition of the present invention is generally buffered to a pH of from about 6.5 to about 10, more preferably from about 6.8 to about 8.0, using one or more suitable biological buffers having a pKa of about 6.0 to about 8.0. These buffers are well known in the art. Illustrative examples of such buffers include, but are not limited to, Tris(hydroxymethyl)aminomethane-HCl (Tris-HCl); 2-[N-morpholino]ethanesulfonic acid (MES); Piperazine-N,N'-bis[2-ethanesulfonic acid] (PIPES); 3-[N-Morpholino]-2-hydroxypropanesulfonic acid (MOPSO), phosphate buffers and the like. Of the biological buffers mentioned above, Tris-HCl is particularly preferred.

The analytic composition may also comprise an organic solvent such as, but not limited to, tetrahydrofuran, acetonitrile, hexane, isomers of hexane, methanol, ethanol, propanol, isopropanol or butanol, and the like. The analytic composition of the present invention may comprise a mixture of organic solvents or a water-organic solvent mixture in any compatible proportion which be can be determined for a particular application as required and as would be will known by those skilled in the art.

In the signal-providing composition of the present invention, the amounts of each component may vary depending upon its intended use, the particular sensitivity of the reagents and other factors well understood by one skilled in the art. Thus, the following general ranges are meant to provide guidance for the skilled worker, and not to limit the practice of the invention.

Specifically, the amount of buffer employed in the present invention is readily apparent to one skilled in the art since it is well known how to determine the quantity of any buffer needed to maintain a desired pH. The amount of signal-generating compound, DPD, is generally at least about 0.01 mMolar, with an amount in the range of from about 0.1 to about 10 mMolar being preferred.

In regard to the second component, i.e. the halogen, pseudohalogen, halogen-providing source or pseudohalogen-providing source, it is normally present in an amount of at least about 0.1 mMolar. More preferably, the halogen, pseudohalogen, halogen-providing source or pseudohalogen-providing source is present in the signal-providing composition of the instant invention in an amount of about 50 to about 100 mMolar.

Regarding the third component, i.e. the peroxide or peroxide-generating reagent composition, that component is present in the signal-providing composition in an amount of at least about 0.02 mMolar. More preferably, the peroxide or peroxide-generating reagent composition is present in an amount of from about 0.5 mMolar to about 1.0 mMolar.

The instant invention also provides a vanadium bromoperoxidase-containing aqueous composition which contains a vanadium bromoperoxidase (VBrPO) in free form, or as a labeled conjugate with a specific binding molecule (such as an antibody, avidin or biotin) and the signal-providing composition described hereinabove. Such a composition can also be buffered as described above for the signal-providing composition of the present invention. The amounts of vanadium bromoperoxidase or vanadium bromoperoxidase-labeled specific binding molecule and signal-providing composition are readily apparent to one skilled in the art.

Besides the compositions described above, the present invention also provides a kit, equipment and instructions useful for carrying out a variety of analytical methods (described below). The packaging of kit components, individually or premixed together, is well known in the art.

In one embodiment, a kit comprises: the signal-providing composition described above, and a vanadium bromoperoxidase or a vanadium bromoperoxidase-labeled specific binding molecule. By "specific binding molecule" it is meant any biological or chemical compound which will specifically bind with a receptor. Particularly useful labeled specific binding species are vanadium bromoperoxidase-labeled proteins or oligonucleotides. Such proteins include antibodies and avidin. Suitable receptors for given specific binding species are well known in the art and are thus not described herein. Other components useful in an assay (such as a surfactant) can be included in the test kit of the instant invention.

Another kit of the instant invention includes only the signal-providing composition of the instant invention.

As used herein, "vanadium bromoperoxidase" is meant to be any vanadium haloperoxidative substance (enzymatic or otherwise) which catalyzes the oxidation of a substance such as luminol to produce an appropriate signal. Specific examples of proteinaceous vanadium bromoperoxidase compounds that may be employed in the instant invention can be found in Butler et al., Chem. Revs., 93, pp. 1937–1944 (1993) and include, but are not limited to the enzymes obtained from *Ascophyllum nodosum, Ceramirum rubrum, Laminaria saccharina, Fucus distichus, Corallina pilulifera, Corallina officinalis, Macrocystis pyrifera* and the like. Of these vanadium bromoperoxidase sources, *Ascophyllum nodosum* is particularly preferred.

Of the non-proteinaceous vanadium bromoperoxidase compounds, those described in Butler et al. above, de Boer, FEBS, 235 pp. 93–97 (1988) and Rehder et al., Inorganica Chom. Acta, 136, L7–L10, 1987; all references herein incorporated, may be used in the present invention. This includes, but is not limited to, VO(Salen) [Salen=oxo-N,N'-bis(salicylidene)ethylenediamine] and VO(MeOX)$_2$ [MeOX=oxobis(2-methylquinoline-8-olato], VO(HSP)(OEt)(HOEt)[HSP=N-(2-hydroxyphenyl salicylidenedieneamine)]. Of these non-proteinaceous vanadium bromoperoxidase compounds, VO(HSP)(OEt)(HOEt) is preferred.

The amount of the vanadium bromoperoxidase employed in the instant invention can vary over a wide range due to the amounts of other components used in the reaction. A useful amount would be readily apparent to one skilled in the art, but a minimum amount would generally be in the femtomolar range.

Another embodiment of the test kit can include the individual components of the signal-providing composition, and any additional optional components as would be readily understood by one skilled in the art. In some methods of this invention, vanadium bromoperoxidase is used in "free form" (non-conjugated) for clinical analysis. In specific binding methods, however, the vanadium bromoperoxidase is used as a conjugate with a specific binding ligand or receptor therefor, or with a specific binding molecule which is reactive with either the ligand or receptor. The ligand and receptor are complexed in such assays and thereby labeled with the vanadium bromoperoxidase for eventual detection of the complex or uncomplexed materials. The preparation of such conjugates can be achieved using a variety of known techniques (for example, see Yoshitake et al., Eur. J. Biochem., 101, 395, 1979, and U.S. Pat. No. 5,106,732 to Kondo et al.).

Various specific binding assay formats are useful in the practice of this invention, and include nucleic acid hybridization assays, immunochemical assays (such as enzyme immunoassays and sandwich assays) and others well known in the art. Such assays are generally described, for example in U.S. Pat. No. 4,598,044, U.S. Pat. No. 4,745,077 to Holian et al., U.S. Pat. No. 5,077,198 to Shih et al., U.S. Pat. No. 5,085,986 to Mauck et al., Matthews et al., Anal. Biochem., 169, pages 1–25 (1988), WO 88/01302 (published Feb. 25, 1988), U.S. Pat. No. 5,082,780 to Warren et al. and U.S. Pat. No. 5,387,510 to Wu.

As stated hereinabove, the present invention further provides a method for producing a detectable signal in response to a vanadium bromoperoxidase comprising: (i) reacting a vanadium bromoperoxidase in the presence of: (a) a chemiluminescent signal-generating reagent comprising a 2,3-dihydro-1,4-phthalazinedione derivative; (b) a halogen, pseudohalogen, halogen- providing source or pseudohalogen-providing source; and (c) a peroxide or a peroxide-generating reagent; to produce a detectable chemiluminescent signal; and (ii) determining the resulting chemiluminescent signal as a measure of the vanadium bromoperoxidase.

The method of the invention can be preceded by an amplification process, such as polymerase chain reaction (commonly known as PCR) as described for example in U.S. Pat. No. 4,965,188 to Mullis et al. and ligase chain reaction which is generally described by Weiss, Science, 251, pages 1292–3, 1991 to increase the amount of targeted nucleic acid which can then be detected using the signal-providing composition of this invention.

Thus, the method of this invention can be used to detect any of a wide variety of chemical and biological materials, such as amino acids, peptides, polypeptides, proteins (including enzymes, avidin, antibodies and antigenic proteins), carbohydrates (including monosaccarides, polysaccharides and lipopolysaccharides), hormones (such as human chorionic gonadotropin, thyroid stimulating hormone, luteinizing hormone, thyroxin, follicle stimulating hormone, parathyroid hormone and growth hormone), metabolites (such as glucose, lactate and pyruvate), oligonucleotides, nucleic acids, vitamins (such as $B_{12}$ and biotin), intact cells from various organisms (including microorganisms) and drugs (narcotics, therapeutic and those abused).

Particularly useful specific binding methods of this invention are those known in the art as sandwich assays whereby the ligand of interest is complexed with at least a first and second receptor either simultaneously or in a desired sequence. One of the receptors is insolublized on a suitable support (such as a microtiter plate; polymeric, magnetic or glass particles; a film; a membrane; a filter paper and others known in the art) by adsorption, covalent or other known attachment procedures, or is capable of being insolubilized through further complexation or reaction. For example, the receptor can be labeled with a specific binding moiety (for example, biotin) which is reactive with its corresponding receptor moiety (for example, avidin) which is insolublized on the support.

In the sandwich assays, the second receptor for the ligand of interest can be labeled with a vanadium bromoperoxidase, or is capable of being so labeled through additional specific binding reactions (such as labeling the ligand through an avidin-biotin complex). Detection of the label is accomplished using the signal-providing composition described above. In more preferred embodiments, the ligand of interest is an antigenic material with which antibodies are reactive, or a nucleic acid with which complementary nucleic acids (such as oligonucleotides) can be hybridized.

The following examples are given to illustrate the scope of this invention. Because these examples are given for illustrative purposes only, the invention embodied therein should not be limited thereto.

Except where noted all reagents and equipment were obtained from Eastman Kodak Company or other commercial sources.

EXAMPLE 1

Preparation of an Aqueous Chemiluminescent Composition

An aqueous composition for providing a chemiluminescent signal was prepared as follows:

A buffer solution (pH 8.0) was prepared, containing 10 $\mu$M of diethylenetriaminepentaacetic acid (DTPA) and 0.01M NaBr in a 0.05M of Tris-HCl buffer.

The signal-providing composition was prepared from a two-part mixture. The first part contained 1.0 mM of Na luminol and the second part contained 1.0 mM $H_2O_2$ both prepared in the above buffer. These two parts were combined immediately before use. A known concentration ranging from about 5 to about 50,000 attomoles of vanadium bromoperoxidase was then added.

The vanadium bromoperoxidase (stock solution; stored at 4° C.) was serially diluted in 0.05M Tris-HCl, pH 8.0, 0.01% bovine serum albumin (BSA). These enzyme solutions were pipetted into opaque microtiter plates containing the signal-providing composition described above.

The chemiluminescent signal of the composition was then measured using a DYNATECH [trademark] ML3000 luminometer at 37° C.

Figure 1:
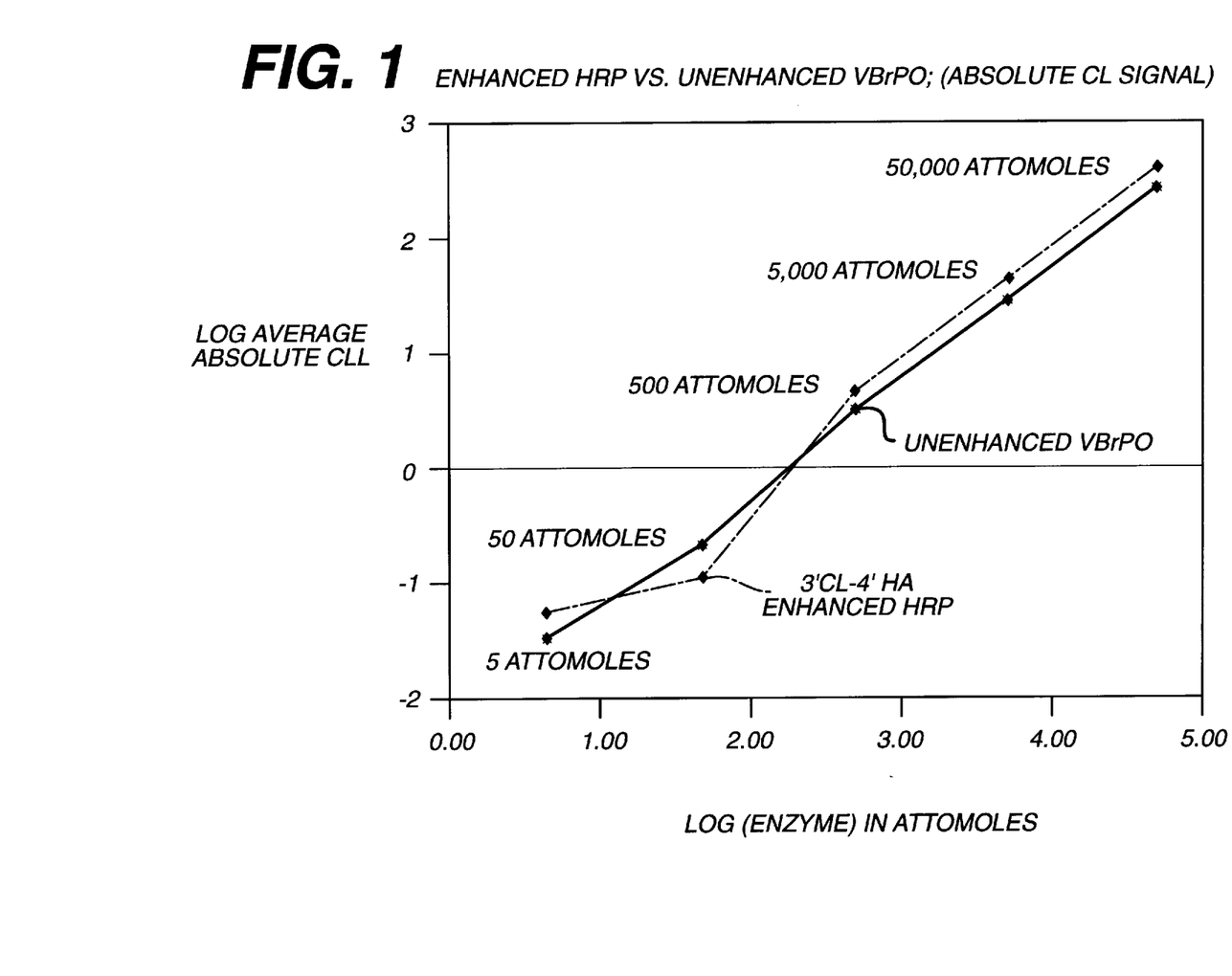
FIG. 1 is a graphical representation of the chemiluminescent signal obtained using a composition of the present invention and a control composition, as described in Example 1 of U.S. Pat. No. 5,372,931.

FIG. 1 shows the chemiluminescent output (1.0 sec integral at t=5.0 minutes) under the above conditions for vanadium bromoperoxidase as well as the signal output for horseradish peroxidase (HRP) using the aqueous chemiluminescent composition of Example 1 of U.S. Pat. No. 5,372,931. This figure shows that the signal-providing composition of the instant invention produces a signal that is comparable to the composition disclosed in U.S. Pat. No. 5,372,931 without the need for enhancers or electron transfer agents which are required in the '931 patent.

Figure 2:
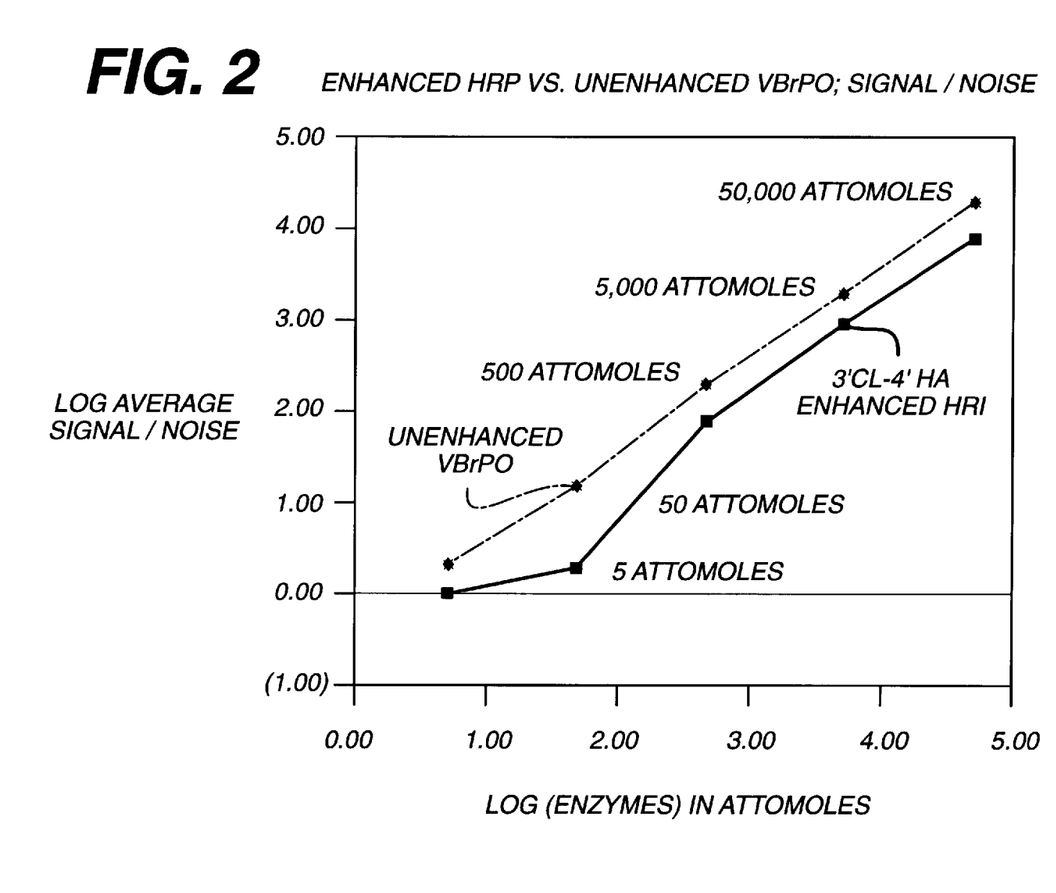
FIG. 2 is a graphical representation of the signal-to-noise response obtained using a composition of the present invention and a control composition, as described in Example 1 of U.S. Pat. No. 5,372,931.

FIG. 2 shows the signal-to-noise response and the added benefit of a much reduced background using the signal-providing composition of the instant invention compared to the composition disclosed in the '931 patent.

The data in Table 1 (in the buffer described above at pH 7.5 and pH 8.0) shows a comparison of the relative chemiluminescent signal generated and the signal-to-noise ratio using the composition of the instant invention. Vanadium bromoperoxidase was compared to the horseradish peroxidase (HRP) enhanced system using either 4-iodophenol (AMERLITE (trademark) system) or 3'chloro-4'-hydroxyacetanilide. The results tabulated in Table 1 indicate that the vanadium bromoperoxidase system of the instant invention can detect enzyme levels that are 10× lower in concentration than the HRP enhanced systems disclosed in the prior art.

EXAMPLE 2
Preparation of an Aqueous Chemiluminescent Composition

An aqueous composition for providing a chemiluminescent signal was prepared as follows:

A buffer solution (pH 7.0) was prepared containing 10 μM of diethylenetriaminepentaacetic acid and 0.05M NaBr in a 0.05M of MES buffer.

The signal-providing composition was prepared from a two-part mixture. The first part contained 1.0 mM of Na luminol and 300 μM of either 3'Cl-4'-hydroxyacetanilide or 4-iodophenol, enhancers. The second part contained 1.0 mM $H_2O_2$ both prepared in the above buffer. These two parts were combined immediately before use. A known concentration ranging from about 5 to about 50,000 attomoles of vanadium bromoperoxidase was then added.

The vanadium bromoperoxidase (stock solution; stored at 4° C.) was serially diluted in 0.05 M Tris-HCl, pH 8.0, 0.01% bovine serum albumin (BSA). These enzyme solutions were pipetted into opaque microtiter plates containing the signal-providing composition described above. In the control case, the first part contained no enhancer.

The chemiluminescent signal of the composition was then measured using a DYNATECH [trademark] ML3000 luminometer at 37° C. using 1.0 sec. integral at t=5.0 minutes.

Table 2 shows that the vanadium bromoperoxidase system of the instant invention is not affected positively by enhancers used in the HRP system.

Figure 3:
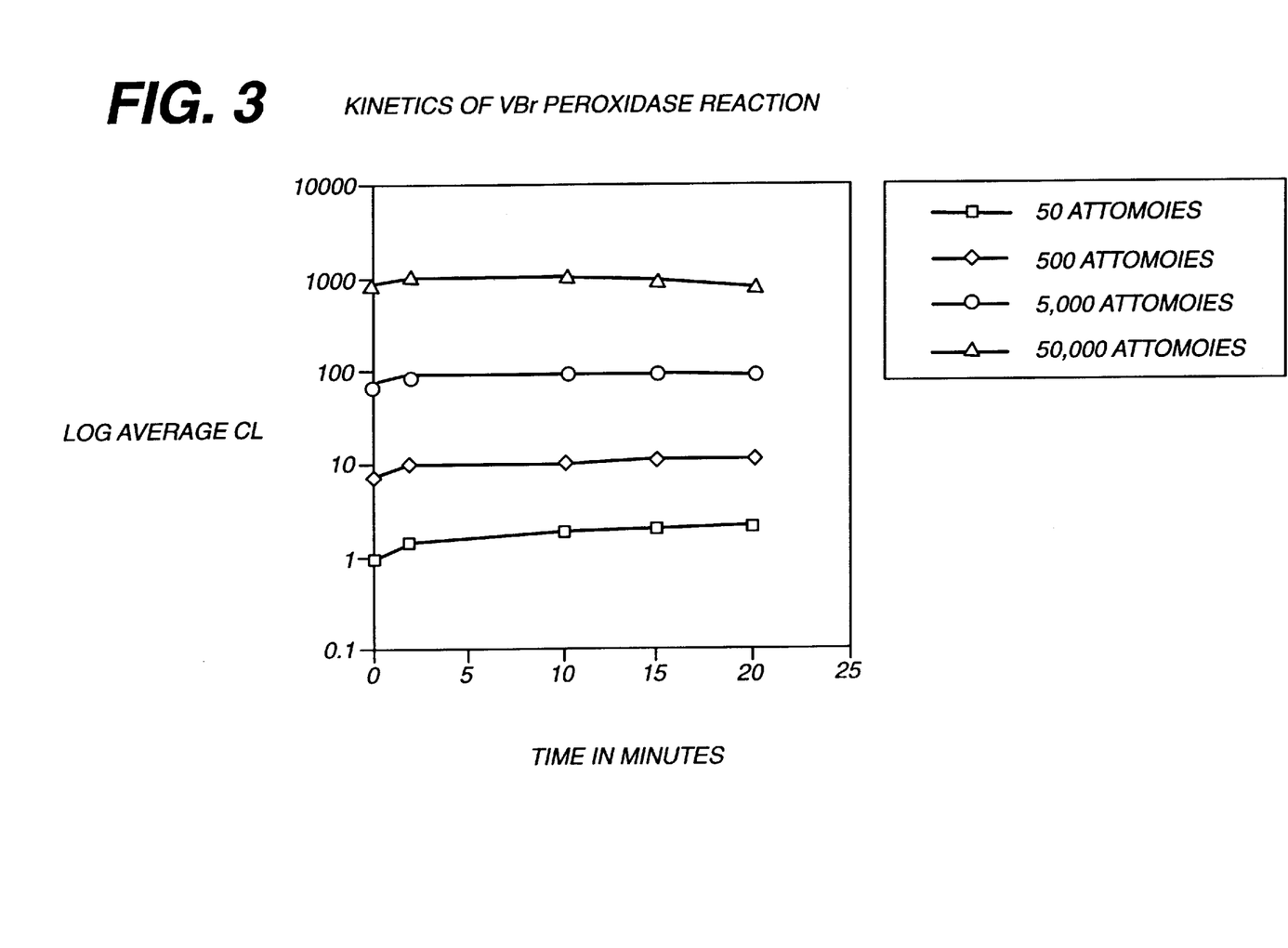
FIG. 3 is a graphical representation of the kinetics of a vanadium bromoperoxidase reaction using the signal-providing composition of the present invention.
Figure 4:
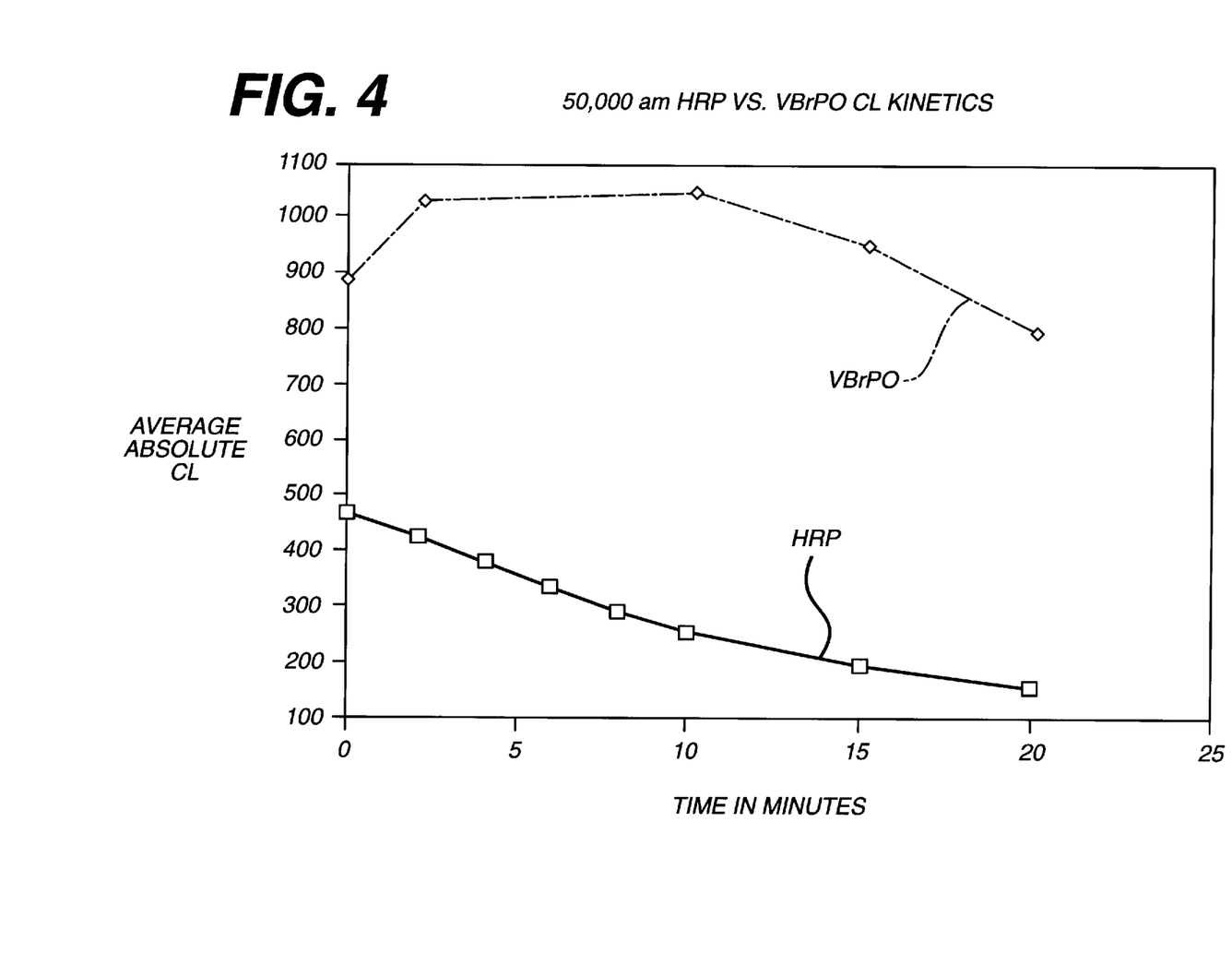
FIG. 4 is a graphical representation of the signal output of an HRP control composition as described in Example 1 of U.S. Pat. No. 5,372,931 at 50,000 attomoles compared to the same concentration of vanadium bromoperoxidase.

Another advantage of the instant invention over the HRP system disclosed in the '931 patent, as shown in FIGS. 3 and 4, is that the kinetics of the system at different concentrations of vanadium bromoperoxidase remains essentially constant over a long period of time. This is clearly illustrated in FIG. 4 whereat it is shown that the signal using the prior art HRP system drastically and immediately tails off whereas the signal generated using the composition of the invention remains fairly constant.

TABLE 1

Comparison of the Chemiluminescent Output from HRP Enhanced by either p-Iodophenol or 3'Chloro-4'HA with the Unenchanced Vanadium Bromoperoxidase

| Emzyme Attomoles 200 μL | HRP[a] CL Signal | HRP[a] S/N | HRP[b] CL Signal | HRP[b] S/N | VBrPO[c] CL Signal | VBrPO[c] S/N | VBrPO[d] CL Signal | VBrPO[d] S/N |
|---|---|---|---|---|---|---|---|---|
| 0.00 | 0.06 | 1 | 0.02 | 1 | 0.014 | 1 | 0.003 | 1 |
| 5.0 | 0.06 | 1 | 0.02 | 1 | 0.031 | 2 | 0.009 | 3 |
| 50.0 | 0.11 | 2 | 0.33 | 16.5 | 0.208 | 15 | 0.079 | 24 |
| 500.0 | 7.69 | 128 | 5.49 | 275 | 2.82 | 197 | 0.900 | 270 |
| 5,000.0 | 230.0 | 3833 | 58.95 | 1326 | 26.51 | 1850 | 8.59 | 2576 |
| 50,000.0 | 2729 | 45480 | 461 | 23050 | 275 | 19216 | 85.42 | 25627 |

[a]Amerlite enhancer system with HRP (PIP)
[b]Enhancer system with HRP (3'Cl-4'HA); Example 1 of U.S. Pat. No. 5,372,931
[c]Vanadium bromoperoxidase at pH 8.0, TRIS-HCl 0.05 M, 500 μM luminol, 500 μM $H_2O_2$, 0.01 M NaBr, 10 μM DTPA, final concentrations.
[d]Vanadium bromoperoxidase at pH 7.5, TRIS-HCl 0.05 M, 500 μM luminol, 500 μM $H_2O_2$, 0.01 M NaBr, 10 μM DTPA, final concentrations.

TABLE 2

Comparison of the Chemiluminescent Unenhanced Vanadium Bromoperoxidase with added p-Iodophenol or 3'C14'HA

| Enzyme Attomoles 200 μL | VBrPO[a] CL (PIP) Signal | VBrPO[a] S/N | VBrPO[b] CL (3') Signal | VBrPO[b] S/N | VBrPO[c] CL (U) Signal | VBrPO[c] S/N | VBrPO[d] CL (U) Signal | VBrPO[d] S/N |
|---|---|---|---|---|---|---|---|---|
| 0.00 | 0.010 | 1 | 0.006 | 1 | 0.010 | 1 | 0.008 | 1 |
| 5.0 | 0.015 | 1 | 0.007 | 1 | 0.015 | 1 | 0.015 | 2 |
| 50.0 | 0.054 | 5 | 0.024 | 4 | 0.054 | 5 | 0.089 | 12 |
| 500.0 | 0.484 | 47 | 0.215 | 36 | 0.502 | 49 | 1.04 | 136 |
| 5,000.0 | 4.940 | 483 | 2.14 | 340 | 5.19 | 508 | 11.63 | 516 |
| 50,000.0 | 33.76 | 3305 | 12.6 | 2101 | 36.79 | 3601 | 106 | 13865 |

[a]MES buffer (0.05 M) pH = 7.0; VBrPO; p-Iodophenol 150 μM; NaBr 0.1 M; 0.5 mM $H_2O_2$; Luminol, 0.5 mM
[b]MES buffer (0.05 M) pH = 7.0; VBrPO; 3'Cl-4'HA 150 μM; NaBr 0.1 M; 0.5 mM $H_2O_2$; Luminol, 0.5 mM
[c]MES buffer (0.05 M) pH = 7.0; VBrPO; NaBr 0.1 M; 0.5 mM $H_2O_2$; Luminol, 0.5 mM
[d]Tris-OH buffer (0.05 M) pH = 7.5; VBrPO; NaBr 0.1 M; 0.5 mM $H_2O_2$; Luminol, 0.5 mM The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

What is claimed is:

1. An analytical composition for providing a chemiluminescent signal having a pH of from about 6.5 to about 10 comprising:
   (a) a chemiluminescent signal-generating reagent which provides a signal in response to the catalytic activity of a vanadium bromoperoxidase, said signal-generating reagent comprising a 2,3-dihydro-1,4-pthalazinedione derivative;
   (b) a halogen, pseudohalogen, halogen-providing source or pseudohalogen-providing source; and
   (c) a peroxide or a peroxide-generating reagent.

2. The analytical composition of claim 1 wherein said halogen-providing source is a metal or non-metal salt.

3. The analytical composition of claim 2 wherein said halogen-providing source is any non-metal salt.

4. The analytical composition of claim 3 wherein said halogen-providing source is ammonium bromide.

5. The analytical composition of claim 2 wherein said halogen-providing source is NaBr.

6. The analytical composition of claim 1 wherein said pseudohalogen-providing source is a Group IA metal compound containing as one of its ligands $CN^-$, $SCN^-$, $OCN^-$, azide or isonitrile.

7. The analytical composition of claim 1 wherein said peroxide-generating reagent is a perborate, peracetate, urea peroxide, peracid, oxone, hydroperoxide or peroxybenzoic acid.

8. The analytical composition of claim 1 further comprising an aqueous mixture.

9. The analytical composition of claim 1 further comprising an organic solvent.

10. The analytical composition of claim 9 wherein the organic solvent is methanol, ethanol, isopropanol, tetrahydrofuran, acetonitrile, hexane, hexane isomers or mixtures thereof.

11. The analytical composition of claim 1 further comprising an aqueous organic solvent mixture.

12. The analytical composition of claim 1 wherein said 2,3-dihydro-1,4-phthalazinedione derivative is luminol, isoluminol, N-(4-aminobutyl)-N-ethylisoluminol hemisuccinimide, N-(6-amino-hexyl)-N-ethylisoluminol, N-ethylisoluminol or 7-dimethylaminonaphthalene-1,2 dicarboxylic acid hydrazide.

13. The analytical composition of claim 12 wherein the 2,3-dihydro-1,4-phthalazinedione derivative is luminol.

14. The analytical composition of claim 1 further comprising a vanadium bromoperoxidase or a vanadium bromoperoxidase-labeled specific binding molecule.

15. The analytical composition of claim 14 wherein said vanadium bromoperoxidase is proteinaceous or non-proteinaceous.

16. The analytical composition of claim 15 wherein said proteinaceous vanadium bromoperoxidase is obtained from *Ascophyllum nodosum, Ceramirum rubrum, Laminaria saccharina, Fucus distichus, Corallina pilulifera, Corallina officinalis* or *Macrocystis pyifera*.

17. The analytical composition of claim 16 wherein said proteinaceous vanadium bromoperoxidase is obtained from *Ascophyllum nodosum*.

18. The analytical composition of claim 15 wherein said non-proteinaceous vanadium bromoperoxidase is VO(Salen), VO(MeOX)$_2$ or VO(HSP)(OEt)(HOEt).

19. The analytical composition of claim 18 wherein said non-proteinaceous vanadium bromoperoxidase is VO(HSP)(OEt)(HOEt).

20. A diagnostic test kit for the determination of an analyte as a result of the catalytic activity of a vanadium bromoperoxidase, said kit comprising
   an analytical composition for providing a chemiluminescent signal having a pH of from about 6.5 to about 10 comprising
      (a) a chemiluminescent signal-generating reagent which provides a signal in response to the catalytic activity of a vanadium bromoperoxidase, said signal-generating reagent comprising a 2,3-dihydro-1,4-pthalazinedione derivative;
      (b) a halogen, pseudohalogen, halogen-providing source or pseudohalogen-providing source; and
      (c) a peroxide or a peroxide-generating reagent.

21. The diagnostic test kit of claim 20 further comprising a vanadium bromoperoxidase or a vanadium bromoperoxidase-labeled specific binding species.

22. The diagnostic test kit of claim 21 wherein said vanadium bromoperoxidase is proteinaceous or non-proteinaceous.

23. The diagnostic test kit of claim 22 wherein the proteinaceous vanadium bromoperoxidase is obtained from *Ascophyllum nodosum, Ceramirum rubrum, Laminaria saccharina, Fucus distichus, Corallina pilulifera, Corallina officinalis* or *Macrocystis pyifera*.

24. The diagnostic test kit of claim 23 wherein said proteinaceous vanadium bromoperoxidase is obtained from *Ascophyllum nodosum*.

25. The diagnostic test kit of claim 22 wherein said non-proteinaceous vanadium bromoperoxidase is VO(Salen), VO(MeOX)$_2$ or VO(HSP)(OEt)(HOEt).

26. The diagnostic test kit of claim 25 wherein said non-proteinaceous vanadium bromoperoxidase is VO(HSP)(OEt)(HOEt).

27. A method for producing a detectable signal in response to a vanadium bromoperoxidase comprising:
   (i) reacting a vanadium bromoperoxidase in the presence of
      (a) a chemiluminescent signal-generating reagent comprising a 2,3-dihydro-1,4-pthalazinedione derivative;
      (b) a halogen, pseudohalogen, halogen-providing source or pseudohalogen-providing source; and
      (c) a peroxide or a peroxide-generating reagent to produce a detectable chemiluminescent signal; and
   (ii) determining the resulting chemiluminescent signal as a measure of the vanadium bromoperoxidase.

28. The method of claim 27 wherein said vanadium bromoperoxidase is present as an analyte or is present in free form for the detection of non-immunological analyte other than the vanadium bromoperoxidase.

29. The method of claim 28 wherein said vanadium bromoperoxidase is detected as part of a conjugate of vanadium bromoperoxidase and a specific binding species.

30. In a specific binding assay for the determination of a specific binding ligand comprising reacting the specific binding ligand with a specific binding partner to form a specific binding complex, and detecting the complex, wherein a peroxidase is used as a label to detect the specific binding complex, and wherein the improvement comprises using a vanadium bromoperoxidase as said label and contacting the vanadium bromoperoxidase-labeled specific binding complex with:

(a) a chemiluminescent signal-generating reagent comprising a 2,3-dihydro-1,4-phthalazinedione derivative;

(b) a halogen, pseudohalogen, halogen-providing source or pseudohalogen-providing source; and (c) a peroxide or a peroxide-generating reagent composition; to produce a detectable chemiluminescent signal.

31. The method of claim 30 wherein said specific binding ligand or said specific binding partner is insolubilized or insolubilizable.

32. The method of claim 30 wherein a second specific binding partner which specifically binds to said specific binding ligand is additionally used in order to form a sandwich of specific binding ligand, wherein said specific binding partner, or said second specific binding partner is insolubilized or insolubilizable.

33. The method of claim 32 for the determination of an antigen as said specific binding ligand, and wherein said specific binding partner and said second specific binding partner are antibodies specific to said antigen.

34. The method of claim 30 for the determination of a nucleic acid wherein said specific binding species are capable of reacting with said nucleic acid.

35. The method of claim 32 for the determination of a nucleic acid wherein said specific binding partner and said second specific binding partner are oligonucleotides which are complementary to different sequences of said nucleic acid.

36. The method of claim 30 further comprising amplifying said nucleic acid before the reacting step.

37. The method of claim 32 wherein said 2,3-dihydro-1,4-phthalazinedione derivative is luminol, isoluminol, N-(4-aminobutyl)-N-ethylisoluminol hemisuccinimide, N-(6-aminohexyl)-N-ethylisoluminol, N-ethylisoluminol or 7-dimethylaminonaphthalene-1,2-dicarboxylic acid hydrazide.

38. The method of claim 37 wherein said 2,3-dihydro-1,4-phthalazinedione derivative is luminol.

39. The method of claim 30 wherein said chemiluminescent signal-generating compound is present in an amount from about 0.01 to about 10 mM; said halogen, pseudohalogen, halogen-providing source or pseudohalogen-providing source is present in an amount of from 0.1 to about 100 mM; and said peroxide or peroxide-generating reagent is present in an amount of from about 0.5 to about 10 mM.

40. An aqueous composition buffered to a pH of from about 6.5 to about 10 comprising:

(a) a vanadium bromoperoxidase-labeled specific binding molecule;

(b) a chemiluminescent signal-generating reagent comprising a 2,3-dihydro-1,4-pthalazinedione derivative;

(c) a halogen, pseudohalogen, halogen-providing source or pseudohalogen-providing source; and (d) a peroxide or a peroxide-generating reagent.

* * * * *